(12) United States Patent
Liu et al.

(10) Patent No.: US 8,084,430 B2
(45) Date of Patent: Dec. 27, 2011

(54) ENT-KAURENE DITERPENE COMPOUND AND ITS DERIVATIVES, THEIR PREPARATION AND THEIR USE

(75) Inventors: Hongmin Liu, Zhengzhou (CN); Wenchen Zhu, Zhengzhou (CN); Chenggong Zhu, Zhengzhou (CN); Qingduan Wang, Zhengzhou (CN); Yu Ke, Zhengzhou (CN); Zhengzhou Liu, Zhengzhou (CN); Xuebin Yan, Zhengzhou (CN); Zhang Jianye, Zhengzhou (CN); Hongli Qu, Zhengzhou (CN)

(73) Assignees: Zhengzhou University, Henan (CN); Furen Pharmaceutical, Henan (CN)

( * ) Notice: Subject to any disclaimer, the term of this patent is extended or adjusted under 35 U.S.C. 154(b) by 553 days.

(21) Appl. No.: 12/160,359

(22) PCT Filed: Jan. 18, 2007

(86) PCT No.: PCT/CN2007/000187
§ 371 (c)(1),
(2), (4) Date: Jul. 9, 2008

(87) PCT Pub. No.: WO2007/082475
PCT Pub. Date: Jul. 26, 2007

(65) Prior Publication Data
US 2010/0228014 A1     Sep. 9, 2010

(30) Foreign Application Priority Data

Jan. 18, 2006  (CN) .......................... 2006 1 0017358

(51) Int. Cl.
*A01N 43/04* (2006.01)
*A61K 31/70* (2006.01)
*C07H 15/24* (2006.01)
*C07D 311/78* (2006.01)

(52) U.S. Cl. .......................... 514/27; 536/18.1; 549/382

(58) Field of Classification Search .................. None
See application file for complete search history.

(56) References Cited

U.S. PATENT DOCUMENTS
6,894,073 B2 * 5/2005 Lee et al. ...................... 514/453

FOREIGN PATENT DOCUMENTS
CN    1255502    6/2000

* cited by examiner

*Primary Examiner* — Traviss C McIntosh, III
(74) *Attorney, Agent, or Firm* — Merchant & Gould P.C.

(57) ABSTRACT

Novel ent-kaurene diterpene compound and its derivatives, their preparation methods and their use. ent-Kaurene diterpene in the present invention could be used as desired intermediates for preparing asymmetric organic compounds and medicaments, and could be used as antitumor agent, anti-inflammatory agent and immune agent etc. The said ent-kaurene diterpene compound could be condensed with hydroxyl compounds to obtain various acetal derivatives, could be reacted with amine compounds to obtain various amino derivatives, and could be reacted with acyl halide or acid anhydride to obtain various acyl derivatives.

10 Claims, No Drawings

ENT-KAURENE DITERPENE COMPOUND AND ITS DERIVATIVES, THEIR PREPARATION AND THEIR USE

1. TECHNICAL FIELD

The present invention relates to a series of organic compounds and methods of preparation, in particular relates to an ent-kaurene diterpenoid compound and its derivatives, and extraction and preparation methods and use thereof.

2. BACKGROUND ART

*Rabdosia rubescens* (Hemls.) Hara (family Labiatae of Isodon), also named Donglingcao in traditional Chinese medicine, contains abounding diterpenoid ingredients. There have been more than 500 kinds of diterpenoids separated from that kind of plant by now, among which many of those having ent-kaurene structure have activities including antibacterial activity, cytotoxic activity, anti-tumor activity, activity in inhibiting the mitochondrial oxidative phosphorylation, insect-antifeeding activity, plant growth regulation activity anti-inflammatory activity, regulation of cardiovascular functions, etc. . . . (S Ttanaba and HNishikawa, JpnJBact, 1954(9), 475; M Yamaguchi, M Taniguchi, I Kubo and T Kubota, Agr Biol Chem, 1977(41), 2475; T Arai, Y Koyama, T Suenaga and T Morita, Chemotherapy, 1962(10), 197; M Taniguchi, M Yamaguchi, I Kubo and T Kubota, Agr Bioi Chem, 1979(43), 71; Li Qi, Chen Zheng, Liu Jie, Sun Handong, Lin Zhongwen, Chinese Pharmacological Bulletin, 1992, 8(1), 3; Li Huilan, Wang Maode, Zhang Zhaojiu, Chinese Drugs Bulletin, 1988, 18(10), 46) As a result, it is valuable in theory and in practice to research those plants, especially an ent-kaurene diterpenoid which has an excellent anti-tumor activity.

The structure of ent-kaurene diterpenoid having an α-exomethylene cyclopentanone unit is represented as follows:

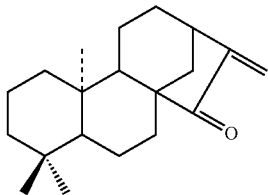

The α-exomethylene cyclopentanone unit in that structure has been determined as the anti-tumor active center of those substances after research. (S Ttanaba and H Nishikawa, Jpn J Bact, 1954 (9), 475; T Arai, YKoyama, T Suenaga and T Morita, J Antibiotics Ser, 1963, A16, 132; I Kubo, M Taniguchi, Y Satomura and T Kubota, Agr Biol Chem, 1974(38), 1261; T Arai, Y Koyama, T Morita and H Kaji, Chemotherapy, 1961(9), 403; I Kubo, M Taniguchi and T Kubota, Rev Latinoamer Quim, 1978(9), 157) Oridonin A is the representative of those having such structure. There are many researches now on oridonin A. Zhang Tanmu researching group from Henan Medical University and Fujita researching group from Japan etc. have all done much pharmacological research on oridonin A. It is assuredly proven that oridonin A has antitumor activity both in vitro and in vivo. It also has a broad antitumor spectra and can effectively kill cells including human nasopharyngeal carcinoma cell, human hepatoma cell, human cervical carcinoma cell, esophageal carcinoma cell etc. . . . . However, due to oridonin A having low stability and water-solubility and difficulty in controlling the quality of oridonin A's extration solution, the development of oridonin A is confined to the extent. We have synthesized a series of glucoside and ester compounds (ZL99101179.3). It has high practical value and meaning in developing the traditional Chinese herbal medicine *R. rubescens* (Donglingcao) to develop a new pharmaceutical compound by using diterpenoid ingredient from *R. rubescens* with a high content and a good anti-tumor activity based on those former research works. We synthesized and found more derivatives having higher anti-tumor activity, less toxicity and better property without destroying its active center structure.

3. CONTENT OF THE INVENTION

The object of the invention is to provide a novel diterpenoid compound extracted from *R. rubescens* and a series of derivatives thereof.

The other object of the invention is to provide the method of extracting this diterpenoid compound and the synthetical method of its derivatives.

The still another object of the invention is to provide the use of this diterpenoid compound and derivatives thereof.

For those aims above, the technical solution of this invention is described as follows:

The raw material of the invention is *R. rubescens* from Jiyuan, China. Under certain conditions of extraction and seperation, the ent-kaurene diterpenoid compound is obtained, which is a new natural diterpenoid reported firstly.

The structure of ent-kaurene diterpenoid of the invention is represented as follows:

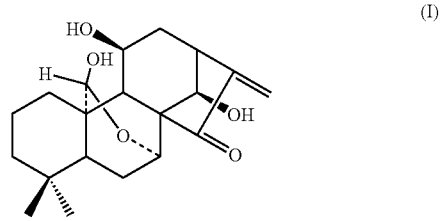

(I)

The extraction and separation methods are as follows:

Impregnating the aerial parts of *R. rubescens* with an extraction solvent. After impregnation at 40~60° C. for 3 hours to 3 days, concentrating to eliminate 85~90% of the solvent, isolating the concentrated solution by LSA-10 type macroporous adsorptive resins and silica gel chromatography repeatedly to give the ent-kaurene diterpenoid. Obtaining the pure ent-kaurene diterpenoid by recrystallization.

Wherein said organic solvent is selected from one of ethanol, methanol, isopropanol, acetone, ethyl acetate or petroleum ether; said solvent in recrystallization is selected from one of methanol, ethanol, acetonitrile, acetone, ethyl acetate, tetrahydrofuran or isopropanol.

Reacting the aforesaid ent-kaurene diterpenoi (I) with the hydroxyl compound gives a compound represented by formula (II).

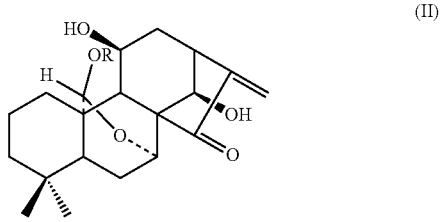

(II)

R = $C_nH_{2n+1}$(n = 1-12), $CH_2CH_2OH$, $CH_2CH_2Cl$, $CH_2CH(OH)CH_2OH$, $CH_2CH_2CH_2OH$, $CH_2CH(OH)CH_3$, $CH_2COOH$
Glucosyl, Galactosyl, Xylosyl, Mannose residues ect.

Compound represented by formula II is prepared specifically by the following method:

An ent-kaurene diterpenoid represented by formula I is dissolved in an organic solvent, which performs a condensation reaction with the hydroxyl compound in the presence of acidic catalysts at 0~100° C. The molar ratio of reactants is 1: 1~100 or the hydroxyl compound is also used as the reaction solvent simultaneously; the reaction time is 1~72 hours, followed by evaporating the solvent to dryness after reaction and recrystallizing to give the compound represented by formula II.

Wherein said organic solvent is selected from one of nitromethane, acetonitrile, ethanol, methanol, isopropanol, 1,2-dichloroethane, trichloroethane, dichloromethane, chloroform, dioxane or tetrahydrofuran; said catalyst used in condensation reaction is selected from one of hydrochloric acid, ammonium chloride, sulfuric acid, ammonium sulfate or p-toluene sulfonic acid; the solvent in said recrystallization is selected from one of acetonitrile, ethanol, methanol, acetone, tetrahydrofuran, isopropanol or ethyl acetate.

Reacting the aforesaid ent-kaurene diterpenoi(I) or derivatives thereof of formula (II) with amino compounds gives a compound represented by formula (III).

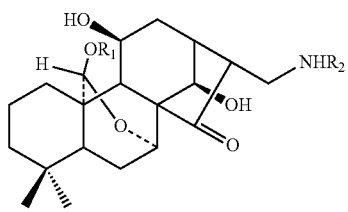

(III)

$R_1$ = H, $CnH_{2n+1}$(n = 1-12), $CH_2CH_2OH$, $CH_2CH_2Cl$ $CH_2CH(OH)CH_2OH$, $CH_2CH_2CH_2OH$, $CH_2CH(OH)CH_3$, $CH_2COOH$
Glucosyl, Galactosyl, Xylosyl, Mannose residues, ect.
$R_2$ = $CnH_{2n+1}$(n = 1-12), o,m,p-Cl—$C_6H_5$, o,m,p-Br—$C_6H_5$, o,m,p-F—$C_6H_5$, $C_6H_5$ Compound represented by formula III is prepared specifically by the following method:

An ent-kaurene diterpenoid represented by formula I or derivatives thereof represented by formula II is dissolved in an organic solvent, which reacts with an amino compound in the presence of acidic catalysts, the molar ratio of reactants is 1: 1~20 and the reaction temperature is controlled at 10~90° C.; The reaction time is 2~72 hours and the reaction is not terminated until the raw material disappears by TLC monitoring, followed by evaporating solvent to dryness; The product represented by formula III is obtained by recrystallization or column chromatography.

Wherein said solvent is selected from one of nitromethane, acetonitrile, ethanol, methanol, isopropanol, 1,2-dichloroethane, trichloroethane, dichloromethane, chloroform, tetrahydrofuran or dioxane; said catalysts used in addition reaction is selected from one of hydrochloric acid, ammonium chloride, sulfuric acid, ammonium sulfate or p-toluene sulfonic acid; said solvent in recrystallization is selected from one of acetonitrile, ethanol, methanol, acetone, tetrahydrofuran, isopropanol or ethyl acetate.

Reacting the aforesaid ent-kaurene diterpenoi (I) or derivatives thereof of formula (II) with anhydride or acyl halide gives a compound represented by formula (IV).

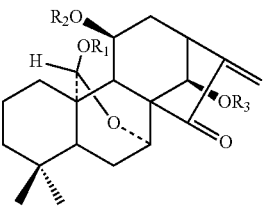

(IV)

$R_1$ = H, $C_nH_{2n+1}$(n = 1-12), $CH_2CH_2OH$, $CH_2CH_2Cl$ $CH_2CH(OH)CH_2OH$, $CH_2CH_2CH_2OH$, $CH_2CH(OH)CH_3$, $CH_2COOH$
Glucosyl, Galactosyl, Xylosyl, Mannose residues, ect.
R2, R3 = H or C1-C12's acyl Compound represented by formula IV is prepared specifically by the following method:

An ent-kaurene diterpenoid represented by formula I or derivatives thereof represented by formula II is dissolved in an organic solvent, which reacts with anhydride or acyl halide in the presence of basic catalysts, the molar ratio of reactants is 1: 1~20; The reaction temperature is controlled at 0·90° C.; The reaction time is 1~72 hours and the reaction is not terminated until the raw material disappears by TLC monitoring, followed by evaporating solvent to dryness; The product is obtained by recrystallization or column chromatography.

Wherein said solvent is selected from one of nitromethane, acetonitrile, 1,2-dichloroethane, trichloroethane, dichloromethane, chloroform, tetrahydrofuran, dioxane, pyridine or triethylamine; said catalysts used in acylation reaction is selected from one or two of sodium methoxide, sodium ethoxide, sodium hydroxide, potassium hydroxide, potassium fluoride, pyridine, diethylamine, triethylamine or 4-N, N-dimethylaminopyridine; said solvent in recrystallization is selected from one of acetonitrile, ethanol, methanol, acetone, tetrahydrofuran, isopropanol or ethyl acetate.

Said ent-kaurene diterpenoid and derivatives thereof described in this invention can be used as an anti-inflammatory agent, an anti-tumor agent and a immunomodulator, also as glycosidase inhibitor, and as drug resistant to other diseases, and as variety of pharmaceutical intermediates, and as an intermediate in chiral synthesis and organic synthesis.

The synthetic method of said ent-kaurene diterpenoid and derivatives thereof in this invention is simple and easy in operation with mild conditions and high yields.

The ent-kaurene diterpenoid extracted by said method has been proven to have a α-exomethylene cyclopentanone unit with a variety of activities, and has hemiacetal structure on 7 and 20 position. The hemiacetal structure on 20 position is very active. It is likely that 11β-OH and 14β-OH can be the binding site with the special enzyme in tumor cells to increase the anti-tumor activity. After primary bioactivity screening, it is found that ent-kaurene diterpenoid and the derivatives synthesized by using it as a substrate all possess high anti-inflammation, anti-tumor, immunoregulation and inhibiting glycosidase activity. The invention provides more candidate compounds for anti-tumor drugs and more development pathways for the Chinese herbal medicine *R. rubescens*. It is believed that the invention will have a better applicable prospect with the development of the biological medicine.

4. EXAMPLES

The present invention will be illustrated with reference to the following examples, which are not deemed to limit the scope of the invention.

Example 1

Extraction and Separation of the ent-kaurene Diterpenoid (Jiyuan Oridonin A)

The aerial part of 3 kg of dried *R. rubescens* was placed into an immersion vessel, and extracted at 50° C. for 3 hours after 40 L of 70% acetone was added. After the extraction is complete, the extract was concentrated to about 3 L, followed by separating roughly the concentrated solution through macroporous resin LSA-10. The portion eluted with 30% acetone was concentrated and then was isolated by silica gel column chromatography repeatedly. Recrystallization was performed with acetone as the solvent to give a pure ent-kaurene diterpenoid.

The experimental data is shown as follows:

White powder solid; Mp 211~212 ° C.; $[\alpha]^D 25$-80.3° (MeOH, c 0.22); $\lambda_{max}$MeOH nm (log $\epsilon$): 233 (3.96); IR $\nu_{max}$KBr cm$^{-1}$: 3590, 3394, 2932, 1722, 1646, 1334, 1254, 1096, 1032 and 990; HR-ESIMS m/z: 371.1829 [M+Na]$^+$ for $C_{20}H_{28}O_5$ (cacld. 371.1834); $^1$H-NMR Spectral Data (400 MHz, DMSO-d$_6$): 2.02 (1H, d, J=12.0 Hz, H-1$\alpha$), 1.29 (1H, m, H-1$\beta$), 1.36 (2H, br s, H-2), 1.06 (1H, m, H-3$\alpha$), 1.42 (1H, d, J=13.4, H-3$\beta$), 1.15 (1H, overlap, H-5$\beta$), 1.52 (1H, m, H-6$\alpha$), 2.63 (1H, t, J=12.0 Hz, H-6$\beta$), 3.94 (1H, d, J=2.9 Hz, H-7$\beta$), 1.14 (1H, d, J=8.4 Hz, H-9$\beta$), 4.60 (1H, q, J=8.4 Hz, H-11$\alpha$), 2.56 (1H, m, H-12$\alpha$), 1.25 (1H, m, H-12$\beta$), 2.78 (1H, d, J=9.1 Hz, H-13$\alpha$), 4.74 (1H, s, H-14$\alpha$), 5.77 (1H, s, H-17a), 5.35 (1H, s, H-17b), 0.82 (3H, s, H-18), 0.90 (3H, s, H-19), 5.69 (1H, s, H-20); $^{13}$C-NMR (400 MHz, DMSO-d$_6$): δ 206.2, 152.9, 115.9, 92.5, 69.6, 64.9, 63.4, 57.7, 56.4, 48.5, 42.8, 42.1, 40.7, 39.6, 33.9, 33.0, 30.7, 24.7, 21.0, 18.0.

Example 2

Preparation of the Derivatives Represented by Formula II (R=CH$_2$CH$_3$)

The ent-kaurene diterpenoid (174 mg, 0.5 mmol) obtained in example 1 was dissolved in ethanol (20 mL), and extracted at 25° C. for 3 hours after 5 mg of p-toluene sulfonic acid was added. The reaction liquid was concentrated after the reaction and recrystallized with methanol to give 190 g of derivative shown by formula II. The yield was 95%.

The experimental data is shown as follows:

White prism solid; Mp 183.2~185.8° C.; $[\alpha]^D 25$-42.0° (c MeOH, 0.22); $\lambda_{max}$MeOH nm (log $\epsilon$): 233 (3.99); IR $\nu_{max}$KBr cm$^{-1}$: 3347, 2958, 2933, 1724, 1645, 1361, 1263, 1099, 1025, 994 and 935; HR-ESIMS m/z: 399.2145 [M+Na]$^+$ for $C_{22}H_{32}O_5$ (cacld. 399.2147); $^1$H-NMR Spectral Data (400 MHz, CDCl$_3$): 2.03 (1H, d, J=11.2 Hz, H-1$\alpha$), 1.37 (1H, overlap, H-1$\beta$), 1.51 (2H, br s, H-2), 1.13 (1H, m, H-3$\alpha$), 1.48 (1H, d, J=13.2, H-3$\beta$), 1.34 (1H, overlap, H-5$\beta$), 1.69 (1H, m, H-6$\alpha$), 2.79 (1H, overlap, H-6$\beta$), 4.07 (1H, d, J=4.0 Hz, H-7$\beta$), 1.41 (1H, d, J=9.6 Hz, H-9$\beta$), 4.41 (1H, q, J=8.8 Hz, H-11$\alpha$), 2.58 (1H, overlap, H-12$\alpha$), 1.25 (1H, overlap, H-12$\beta$), 2.97 (1H, d, J=9.4 Hz, H-13$\alpha$), 4.85 (1H, s, H-14$\alpha$), 6.03 (1H, s, H-17a), 5.41 (1H, s, H-17b), 0.86 (3H, s, H-18), 0.96 (3H, s, H-19), 5.21 (1H, s, H-20), 3.84 (1H, m, H-21a), 3.42 (1H, m, H-21b), 1.23 (3H, s, H-22); $^{13}$C-NMR (400 MHz, CDCl$_3$): δ 205.3, 150.8, 117.5, 99.8, 71.5, 66.3, 65.2, 63.9, 58.1, 56.8, 48.4, 42.0, 41.4, 40.5, 39.8, 34.0, 32.8, 30.5, 24.6, 20.9, 18.2, 15.4.

Example 3

Preparation of the Derivatives Represented by Formula II (R=(CH$_2$)$_7$CH$_3$ The ent-kaurene diterpenoid (174 mg, 0.5 mmol) obtained in example 1 was dissolved in THF (20 mL), which reacted at 25° C. for 36 hours after n-octanol (400 mg, 3.1 mmol) and 5 mg of p-toluene sulfonic acid were added. The reaction solution was concentrated and recrystallized with methanol after reaction to give 145 mg of derivative shown by formula II. The yield was 63%.

The experimental data is shown as follows:

White prism solid; Mp 198.5~201.3° C.; $[\alpha]^D 25$-40.8° (cMeOH, 0.25); $\lambda_{max}$MeOH nm (log $\epsilon$): 235 (3.92); IR $\nu_{max}$KBr cm$^{-1}$: 3354, 2961, 2925, 1730, 1645, 1358, 1267, 1094, 1019, 991 and 933; HR-ESIMS m/z: 481.2935 [M+Na]$^+$ for $C_{28}H_{42}O_5$ (cacld. 481.2930); $^1$H-NMR Spectral Data (400 MHz, CDCl$_3$): 2.01 (1H, d, J=11.2 Hz, H-1$\alpha$), 1.35 (1H, overlap, H-1$\beta$), 1.49 (2H, br s, H-2), 1.11 (1H, m, H-3$\alpha$), 1.46 (1H, d, J=13.2, H-3$\beta$), 1.32 (1H, overlap, H-5$\beta$), 1.67 (1H, m, H-6$\alpha$), 2.77 (1H, overlap, H-6$\beta$), 4.05 (1H, d, J=4.0 Hz, H-7$\beta$), 1.38 (1H, d, J=9.6 Hz, H-9$\beta$), 4.40 (1H, q, J=8.8 Hz, H-11$\alpha$), 2.58 (1H, overlap, H-12$\alpha$), 1.23 (1H, overlap, H-12$\beta$), 2.95 (1H, d, J=9.4 Hz, H-13$\alpha$), 4.83 (1H, s, H-14$\alpha$), 6.01 (1H, s, H-17a), 5.40 (1H, s, H-17b), 0.82 (3H, s, H-18), 0.92 (3H, s, H-19), 5.21 (1H, s, H-20), 3.82 (1H, m, H-21a), 3.39 (1H, m, H-21b), 1.21 (3H, s, H-22); $^{13}$C-NMR (400 MHz, CDCl$_3$): δ 205.4, 150.8, 117.7, 99.9, 71.7, 66.4, 65.4, 64.0, 58.3, 57.1, 48.6, 42.2, 41.5, 40.7, 40.1, 34.2, 32.9, 30.7, 24.8, 21.1, 18.4, 15.6.

Example 4

Preparation of the Derivative Represented by Formula II (R=C$_6$H$_{11}$O$_5$)

The ent-kaurene diterpenoid (174 mg, 0.5 mmol) obtained in example 1 was dissolved in THF (20 mL), which reacted at 25° C. for 3 days after anhydrous glucose (900 mg, 5 mmol) and 5 mg p-toluene sulfonic acid were added. The reaction liquid was extracted with chloroform after reaction, followed by concentrating the extract and recrystallizing with methanol to give 142 mg of derivative represented by formula II. The yield was 55%.

The experimental data is shown as follows:

White powder solid; Mp 165.5~169.0° C.; $[\alpha]^D 25$-53.8° (c MeOH, 0.27); $\lambda_{max}$MeOH nm (log $\epsilon$): 233 (4.10); IR $\nu_{max}$KBr cm$^{-1}$: 3392, 2970, 2929, 1732, 1646, 1371, 1272, 1088, 1013, 985 and 931; HR-ESIMS m/z: 533.2357 [M+Na]$^+$ for $C_{26}H_{38}O_{10}$ (cacld. 533.2363); $^1$H-NMR Spectral Data (400 MHz, DMSO): 2.07 (1H, d, J=11.2 Hz, H-1$\alpha$), 1.40 (1H, overlap, H-1$\beta$), 1.55 (2H, br s, H-2), 1.18 (1H, m, H-3$\alpha$), 1.53 (1H, d, J=13.2, H-3$\beta$), 1.38 (1H, overlap, H-5$\beta$), 1.73 (1H, m, H-6$\alpha$), 2.84 (1H, overlap, H-6$\beta$), 4.11 (1H, d, J=4.0 Hz, H-7$\beta$), 1.45 (1H, d, J=9.6 Hz, H-9$\beta$), 4.45 (1H, q, J=8.8 Hz, H-11$\alpha$), 2.64 (1H, overlap, H-12$\alpha$), 1.29 (1H, overlap, H-12$\beta$), 3.03 (1H, d, J=9.4 Hz, H-13$\alpha$), 4.90 (1H, s, H-14$\alpha$), 6.08 (1H, s, H-17a), 5.43 (1H, s, H-17b), 0.88 (3H, s, H-18), 0.96 (3H, s, H-19), 5.25 (1H, s, H-20), 3.81 (1H, d, J=11.6 Hz, H-6'), 3.59 (1H, dd, J=11.2, 4.8 Hz, H-6'), 3.35-3.17 (4H, m, H-3', H-4', H-5', H-2'); $^{13}$C-NMR (400 MHz, CDCl$_3$): 206.9, 153.1, 116.1, 99.8, 92.7, 77.5, 73.5, 71.8, 70.0, 69.8, 65.4, 63.6, 63.1, 57.9, 56.6, 48.7, 43.0, 42.3, 40.9, 39.7, 34.0, 33.1, 30.9, 24.9, 21.2, 18.1.

Example 5

Preparation of the Derivative Represented by Formula III (R$_1$=CH$_2$CH$_3$, R$_2$=C$_6$H$_5$)

The ent-kaurene diterpenoid derivative (200 mg, 0.5 mmol) obtained in example 2 was dissolved in tetrahydrofuran (15 mL), aniline (56 mg, 0.6 mmol) and 2 mg p-toluene sulfonic acid as a catalyst were added in turn and stirred at 50° C. for 24 hours. The reaction solution was concentrated after reaction and recrystallized with methanol to give 210 mg of derivative represented by formula III. The yield was 89%. The experimental data is shown as follows:

White powder solid; Mp 175.5~177.5° C.; $[\alpha]^D 25$-72.3° (c MeOH, 0.22); $\lambda_{max}$MeOH nm (log $\epsilon$): 230 (3.95); IR $\nu_{max}$KBr cm$^{-1}$: 3595, 3452, 2955, 1747, 1589, 1512, 1453, 1376, 1273, 702; HR-ESIMS m/z: 492.2730 [M+Na]$^+$ for $C_{28}H_{39}NO_5$ (cacld. 492.2726); $^1$H-NMR Spectral Data (400 MHz, DMSO-d$_6$): 2.03 (1H, d, J=12.0 Hz, H-1α), 1.27 (1H, m, H-1β), 1.36 (2H, overlap, H-2), 1.07 (1H, m, H-3α), 1.45 (1H, d, J=13.4, H-3β), 1.15 (1H, d, J=12 Hz, H-5β), 1.54 (1H, m, H-6α), 2.65 (1H, overlap, H-6β), 3.98 (1H, m, H-7β), 1.10 (1H, s, H-9β), 4.57 (1H, q, J=8.4 Hz, H-11α), 2.44 (1H, m, H-12α), 1.23 (1H, m, H-12β), 2.89 (1H, m, J=9.1 Hz, H-13α), 4.64 (1H, s, H-14α), 3.56 (1H, m, H-16), 4.00 (1H, m, H-17a), 3.49 (1H, m, H-17b), 0.83 (3H, s, H-18), 0.90 (3H, s, H-19), 5.63 (1H, s, H-20), 3.81, 3.37 (each 1H, m, H-21), 1.20 (3H, s, H-22), 6.56 (2H, d, J=8.0 Hz, H-2'), 7.06 (2H, t, J=8.0 Hz, H-3'), 6.50 (1H, t, J=7.2 Hz, H-4'); $^{13}$C-NMR (400 MHz, DMSO-d$_6$): δ 206.2, 149.0, 129.1, 115.5, 112.1, 98.6, 67.3, 65.6, 64.2, 63.1, 57.8, 55.6, 49.0, 43.2, 40.1, 39.8, 38.5, 37.8, 34.0, 33.3, 30.8, 28.7, 24.9, 21.3, 18.2, 16.2.

Example 6

Preparation of the Derivative Represented by Formula III ($R_1$=Glucosyl, $R_2$=$C_6H_{13}$)

The ent-kaurene diterpenoid derivative (255 mg, 0.5 mmol) obtained in example 2 was dissolved in tetrahydrofuran (15 mL), n-hexylamine (60 mg, 0.6 mmol) and 2 mg p-toluene sulfonic acid as a catalyst were added in turn and stirred at 50° C. for hours. The reaction liquid was concentrated and recrystallized with methanol to give 210 mg of derivative represented by formula III The yield was 71%.
The experimental data is shown as follows:

White solid powder; Mp 154.6~157.2° C.; $[\alpha]^D 25$-75.5° (c MeOH, 0.25); $\lambda_{max}$MeOH nm (log $\epsilon$): 235 (4.05); IR $\nu_{max}$KBr cm$^{-1}$: 3601, 3395, 3460, 2975, 1753, 1646, 1607, 1371, 1272, 991 and 942; HR-ESIMS m/z: 634.3562 [M+Na]$^+$ for $C_{32}H_{53}NO_{10}$ (cacld. 634.3567); $^1$H-NMR Spectral Data (400 MHz, DMSO-d6): 2.05 (1H, d, J=12.0 Hz, H-1α), 1.29 (1H, m, H-1β), 1.38 (2H, overlap, H-2), 1.09 (1H, m, H-3α), 1.46 (1H, d, J=13.4, H-3β), 1.17 (1H, d, J=12 Hz, H-5β), 1.57 (1H, m, H-6α), 2.67 (1H, overlap, H-6β), 4.00 (1H, m, H-7β), 1.12 (1H, s, H-9β), 4.59 (1H, q, J=8.4 Hz, H-11α), 2.45 (1H, m, H-12α), 1.26 (1H, m, H-12β), 2.90 (1H, m, J=9.1 Hz, H-13α), 4.66 (1H, s, H-14α), 3.58 (1H, m, H-16), 4.02 (1H, m, H-17a), 3.51 (1H, m, H-17b), 0.85 (3H, s, H-18), 0.92 (3H, s, H-19), 5.25 (1H, s, H-20), 3.83 (1H, d, J=11.6 Hz, H-6'), 3.62 (1H, dd, J=11.2, 4.8 Hz, H-6'), 3.38-3.15 (4H, m, H-3', H-4', H-5', H-2'), 2.58 (2H, m, H-1"), 1.45 (2H, m, H-2"), 1.31-1.36 (6H, m, H-3", H-4", H5"), 0.98 (3H, t, J=7.0 Hz, H-6"); $^{13}$C-NMR (400 MHz, DMSO-d$_6$): δ207.0, 99.9, 92.7, 77.6, 73.5, 71.8, 70.0, 69.8, 65.4, 63.6, 63.1, 57.9, 56.6, 53.4, 50.1, 43.0, 42.3, 41.0, 40.5, 39.8, 39.7, 34.0, 33.2, 31.6, 30.9, 30.8, 26.9, 25.0, 22.9, 21.2, 18.1, 14.2.

Example 7

Preparation of the Derivative Represented by Formula IV ($R_3$=H, $R_2$, $R_3$=$C_2H_3O$)

The ent-kaurene diterpenoid (174 g, 0.5 mmol) was dissolved in pyridine (20 mL), acetic anhydride 2 ml (21 mmol) was added and stirred at 80° C. for 10 hours. The temperature was reduced to 20° C. with an ice-water bath. Saturated NaHCO$_3$ solution was added while stirring until the air bubbles were no longer released. The reaction solution was extracted 3 times with ethyl acetate. The organic layer was washed with water repeatedly, dried over anhydrous NaSO$_4$, evaporated to dryness under reduced pressure and recrystallized with ethanol:water (3:1) to give 183 mg of white solid. The yield was 81%.

The experimental data is shown as follows:

White powder solid; Mp 163.5~166° C.; $[\alpha]^D 25$-68.5° (c MeOH, 0.25); $\lambda_{max}$MeOH nm (log $\epsilon$): 235 (4.02); IR $\nu_{max}$KBr cm$^{-1}$: 3592, 3352, 2964, 2938, 1738, 1734, 1724, 1648, 1361, 1284, 1247, 1157, 1118, 1081, 1040 and 1007; HR-ESIMS m/z: 455.2049 [M+Na]$^+$ for $C_{24}H_{32}O_7$ (cacld. 455.2046); $^1$H-NMR Spectral Data (400 MHz, CDCl$_3$): 2.01 (1H, d, J=11.2 Hz, H-1α), 1.38 (1H, overlap, H-1β), 1.53 (2H, br s, H-2), 1.09 (1H, m, H-3α), 1.51 (1H, d, J=13.2, H-3β), 1.35 (1H, overlap, H-5β), 1.69 (1H, m, H-6α), 2.75 (1H, overlap, H-6β), 4.09 (1H, d, J=4.0 Hz, H-7β), 1.40 (1H, d, J=9.6 Hz, H-9β), 4.56 (1H, q, J=8.8 Hz, H-11α), 2.61 (1H, overlap, H-12α), 1.25 (1H, overlap, H-12β), 3.01 (1H, d, J=9.4 Hz, H-13α), 4.93 (1H, s, H-14α), 6.05 (1H, s, H-17a), 5.45 (1H, s, H-17b), 0.86 (3H, s, H-18), 0.96 (3H, s, H-19), 5.67 (1H, s, H-20), 2.15 (3H, s, H-22), 2.08 (3H, s, H-24); $^{13}$C-NMR (400 MHz, CDCl$_3$): δ 205.8, 170.5, 169.3, 148.5, 114.9, 93.2, 68.5, 64.1, 62.5, 58.2, 56.2, 47.8, 42.5, 41.6, 41.2, 39.9, 33.3, 33.0, 30.7, 24.7, 21.0, 20.5, 19.9, 18.3.

Example 8

Preparation of the Derivative Represented by Formula IV ($R_1$=$CH_3$, $R_2$=$C_8H_{15}$O, $R_3$=H)

The ent-kaurene diterpenoid (181 mg, 0.5 mmol) was dissolved in pyridine (20 mL), n-caprylic acid (145 mg, 1 mmol) was added and stirred at 80° C. for 24 hours. The temperature was reduced to 20° C. with an ice-water bath. Saturated NaHCO$_3$ solution was added while stirring until the air bubbles were no longer released. The reaction solution was extracted 3 times with ethyl acetate, The organic layer was washed with water repeatedly, dried over anhydrous NaSO$_4$, evaporated to dryness under reduced pressure and recrystallized with ethanol:water (4:1) to give 170 mg white solid. The yield was 70%.

The experimental data is shown as follows:

White acicular crystal; Mp 231~234° C.; $[\alpha]^D 25$-55.8° (c MeOH, 0.22); $\lambda_{max}$MeOH nm (log $\epsilon$): 242 (4.15); IR $\nu_{max}$KBr cm$^{-1}$: 3603, 3426, 2939, 1733, 1718, 1644, 1263, 1106, 1032, 942, 747 and 615; HR-ESIMS m/z: 511.3028 [M+Na]$^+$ for $C_{29}H_{44}O_6$ (cacld. 511.3036); $^1$H-NMR Spectral Data (400 MHz, CDCl$_3$): 1.98 (1H, d, J=12.0 Hz, H-1α), 1.34 (1H, dd, J=12.0, 4.0 Hz, 1β), 1.36 (2H, br s, H-2), 1.42 (1H, d, J=13.2 Hz, H-3α), 1.07 (1H, dt, J=13.2, 4.0 Hz, H-3β), 1.19 (1H, m, H-5β), 1.57 (1H, m, H-6a), 2.66 (1H, t, J=12.6 Hz, H-6β), 3.98 (1H, d, J=2.8 Hz, H-7β), 1.17 (1H, d, J=9.2 Hz, H-9β), 4.41 (1H, q, J=8.8 Hz H-11α), 2.58 (1H, dt, J=14.0, 9.2 Hz, H-12α), 1.25 (1H, dd, J=14.0, 8.4 Hz, H-12β), 2.80 (1H, d, J=9.2 Hz, H-13α), 4.49 (1H, s, H-14α), 5.78, 5.36 (each 1H, s, H-17), 0.90 (3H, s, H-18), 0.93 (3H, s, H-19), 5.01 (1H, s, H-20), 3.32 (3H, s, H-21), 2.23 (2H, m, H-2'), 1.67 (2H, m, H-3'), 1.28-1.33 (8H, m, H-4'-H7'), 0.91 (3H, t, J=6.8 Hz, H-8'); $^{13}$C NMR (CDCl$_3$): 206.0, 175.2, 152.6, 116.1, 100.6, 69.7, 65.3, 63.3, 57.5, 56.4, 55.1, 48.6, 42.7, 42.0, 40.6, 39.6, 34.6, 33.9, 32.9, 32.2, 30.3, 29.4, 29.4, 25.5, 24.5, 23.1, 20.9, 18.0, 15.0.

Experiment 1

The Experiment Aiming at Research on the Activity Against Esophageal Carcinoma Ec109 Cell of Compounds of the Present Invention

TABLE 1 activity against esophageal carcinoma Ec109 cells of compounds of the invention

| | Name of Compounds | | |
|---|---|---|---|
| | Jiyuan oridonin A | derivative 1 FIG. (II) (R = CH$_3$) | derivative 2 FIG. (II) (R = CH$_2$CH$_3$) |
| IC50 (ug/mL) | 4.52 | 3.96 | 2.43 |

Activity testing method is shown as follows:

Human esophageal carcinoma Ec109 cells were taken as target cells (Henan Institute of Medical Sciences), which were cultured in RPMI1640 medium (GIBCO) with 10% fetal bovine serum (TBD) at 37° C., in 5% $CO_2$. The cells in logarithmic growth phase were inoculated in a 96-well plate, each well containing 6×10$^3$ cells. After 24 hours culture, the Jiyuan oridonin A (the compound obtained in example 1), derivative 1 and derivative 2 in different concentrations were added. After continuous 48 hours culture, the medical solution was removed carefully by absorption, followed by washing with RPMI 1640 medium without fetal bovine serum 3 times. 200 µL of medium with 0.2 mg/mL MTT were added in each well and incubated at 37° C. for 4 hours. The supernatant was removed and 200 µL of DMSO was added. After 10 min of shaking, the colorimetric method was used to determine the OD value of the control group and sample groups by an enzyme-labeling instrument with a detection wavelength of 570 nm, and a reference wavelength of 450 nm. The inhibition rate against cells of drugs in different concentrations was calculated and hemi-inhibitory concentration IC50 (µg/mL) was calculated based on cell inhibition curve.

Conclusion: Jiyuan oridonin A and its 20-methoxy derivative, 20-ethoxy derivative all have a higher cytotoxic activity against Ec109 cell, among which the Jiyuan oridonin A has the highest activity.

Experiment 2

Inhibitory Activity Against Glycosidase of Compounds of the Invention

TABLE 2

Inhibitory activity against glycosidase of compounds of the invention

| Name of Compounds | α-glucosidase | β-glucosidase |
|---|---|---|
| Jiyuan oridonin A | 26.3 | 25.0 |
| derivative 1 FIG. (II) (R = CH$_3$) | 31.0 | 24.2 |
| derivative 2 FIG. (II) (R = CH$_2$CH$_3$) | 33.5 | 26.7 |

*Inhibitory activity was measured with compound concentration of 1 mM.

The inhibitory activity against glycosidase was measured as follows:

40 µl compounds (preparing 0.25 mM solution containing 10 DMSO with 0.067 M potassium phosphate buffer solution in primary screening; preparing solutions containing 10% DMSO with a series of concentration gradients using 0.067 M potassium phosphate buffer solution in IC$_{50}$ testing) and 40 µl 0.1 u/ml glycosidase (baker's yeast, US Sigma) were added in each well of a 96-well plate. After keeping at 37° C. for 40 min, the reaction substrate, p-nitrophenyl glucoside (2.5 mM, 20 µl), was added in each well, and kept at 37° C. for 5 min. The reaction was terminated by addition of buffer, 0.1 M $Na_2CO_3$ 100 µl, and the OD value was determined at 405 nm by colorimetric method. 0.067M phosphate buffer containing 10% DMSO was used instead of the compounds in negative control group. Inhibition rate=(1−OD value of experimental group/OD value of negative control group)×100%, the IC50 value was calculated by drawing.

Conclusion: Jiyuan oridonin. A and its 20-methoxy derivative, 20-ethoxy derivative all have certain inhibitory activity against α- and β-glucosidase in vitro.

5. INDUSTRIAL APPLICABILITY

The invention uses *R. rubescens* from Jiyuan, China as a raw material, which is extracted and separated to give ent-kaurene diterpenoid. Then the diterpenoid performs a condensation reaction with hydroxyl compound to give a variety of acetal derivatives; it also performs reaction with amino compound to give a variety of amino derivatives; it performs reaction with anhydride or acyl halide to give a variety of acylation derivatives. The ent-kaurene diterpenoid and its derivatives can be used as anti-inflammatory agent, anti-tumor agent and immunomodulator, also as glycosidase inhibitor, as medicament resistant to other diseases, as a variety of pharmaceutical intermediates, and as an intermediate in chiral synthesis and organic synthesis.

What is claimed is:

1. An isolated ent-kaurene diterpenoid, having a structure formula as follows:

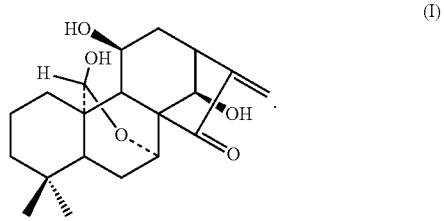

(I)

2. An ent-kaurene diterpenoid derivative, having the structure formula as follows:

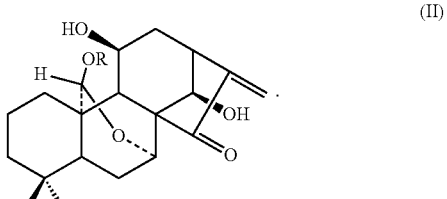

(II)

R = CnH$_{2n+1}$(n = 1-12), CH$_2$CH$_2$OH, CH$_2$CH$_2$Cl, CH$_2$CH(OH)CH$_2$OH, CH$_2$CH$_2$CH$_2$OH, CH$_2$CH(OH)CH$_3$, CH$_2$COOH
Glucosyl, Galactosyl, Xylosyl, or Mannose residues.

3. An ent-kaurene diterpenoid derivative, having a structure general formula as follows:

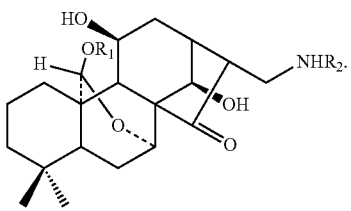

(III)

$R_1$ = H, CnH$_{2n+1}$(n = 1-12), CH$_2$CH$_2$OH, CH$_2$CH$_2$Cl CH$_2$CH(OH)CH$_2$OH, CH$_2$CH$_2$CH$_2$OH, CH$_2$CH(OH)CH$_3$, CH$_2$COOH
Glucosyl, Galactosyl, Xylosyl, Mannose residues, $R_2$ = CnH$_{2n+1}$(n = 1-12), o,m,p-Cl—C$_6$H$_5$, o,m,p-Br—C$_6$H$_5$, o,m,p-F—C$_6$H$_5$, C$_6$H$_5$ 4. An ent-kaurene diterpenoid derivative, having a structure general formula as follows:

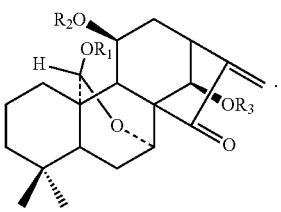

(IV)

$R_1$ = H, $C_nH_{2n+1}$(n = 1-12), CH$_2$CH$_2$OH, CH$_2$CH$_2$Cl CH$_2$CH(OH)CH$_2$OH, CH$_2$CH$_2$CH$_2$OH, CH$_2$CH(OH)CH$_3$, CH$_2$COOH
Glucosyl, Galactosyl, Xylosyl, or Mannose residues,
$R_2$ and $R_3$ being independently H or a $C_1$-$C_{12}$ acyl group 5. A method of extracting the ent-kaurene diterpenoid according to claim 1, comprising the following steps:
Impregnating the aerial parts of R. rubescens with an extraction solvent, wherein said extraction solvent is selected from one of ethanol, methanol, isopropanol, acetone, ethyl acetate or petroleum ether;
After impregnation at 40~60° C. for 3 hours to 3 days, concentrating to eliminate 85~90% solvent, isolating the concentrated solution by LSA-10 type macroporous adsorptive resins and silica gel chromatography repeatedly; then recrystallizing, wherein said solvent in recrystallization is selected from one of methanol, ethanol, acetonitrile, acetone, ethyl acetate, tetrahydrofuran or isopropanol.

6. A method of synthesizing the ent-kaurene diterpenoid derivative according to claim 2, comprising the following steps:
dissolving an ent-kaurene diterpenoid represented by formula I into an organic solvent, wherein said organic solvent is selected from one of nitromethane, acetonitrile, ethanol, methanol, isopropanol, 1,2- dichloroethane, trichloroethane, dichloromethane, chloroform, dioxane or tetrahydrofuran, which performs a condensation reaction with hydroxyl compound in the presence of acidic catalysts at 0~100° C., the molar ratio of reactants is 1: 1~100 or the hydroxyl compound is also used as the reaction solvent simultaneously; the reaction time being 1~72 hours, followed by evaporating the solvent to dryness after reaction and recrystallizing, wherein said solvent in recrystallization is selected from one of acetonitrile, ethanol, methanol, acetone, tetrahydrofuran, isopropanol or ethyl acetate.

7. A method of synthesizing the ent-kaurene diterpenoid derivative according to claim 3, comprising the following steps:
dissolving an ent-kaurene diterpenoid represented by formula I or derivatives thereof represented by formula II into an organic solvent, wherein said solvent is selected from one of nitromethane, acetonitrile, ethanol, methanol, isopropanol, 1,2-dichloroethane, trichloroethane, dichloromethane, chloroform, tetrahydrofuran or dioxane, which reacts with amino compound in the presence of acidic catalysts, the molar ratio of reactants is 1: 1~20; the reaction temperature being controlled at 10~90° C.; the reaction time being 2~72 hours and the reaction is not terminated until the raw material reacts completely which is confirmed by TLC monitoring, followed by evaporating solvent to dryness; the compound represented by formula III being obtained by recrystallization or column chromatography, wherein said solvent in recrystallization is selected from one of acetonitrile, ethanol, methanol, acetone, tetrahydrofuran or ethyl acetate.

8. A method of synthesizing the ent-kaurene diterpenoid derivative according to claim 1, comprising the following steps:
dissolving an ent-kaurene diterpenoid represented by formula I or derivatives thereof represented by formula II into an organic solvent, wherein said solvent is selected from one of nitromethane, acetonitrile, 1,2-dichloroethane, trichloroethane, dichloromethane, chloroform, tetrahydrofuran, dioxane, pyridine or triethylamine, which reacts with anhydride or acyl halide in the presence of basic catalysts, the molar ratio of reactants is 1: 1~20; the reaction temperature is controlled at 0~90° C.; the reaction time being 1~72 hours and the reaction not being terminated until the raw material disappears by TLC monitoring, followed by evaporating solvent to dryness; the compound being obtained by recrystallization or column chromatography, wherein said solvent in recrystallization is selected from one of acetonitrile, ethanol, methanol, acetone, tetrahydrofuran, isopropanol or ethyl acetate.

9. A synthetic method of synthesizing the ent-kaurene diterpenoid derivative according to claim 6 wherein said acidic catalysts is selected from one of hydrochloric acid, ammonium chloride, sulfuric acid, ammonium sulfate or p-toluene sulfonic acid; said basic catalyst is selected from one of sodium methoxide, sodium ethoxide, sodium hydroxide, potassium hydroxide, potassium fluoride, pyridine, diethylamine, triethylamine or 4-N, N-dimethylaminopyridine.

10. A method of treating esophageal cancer or inhibiting glycosidase, comprising administering an effective amount of the ent-kaurene diterpenoid of claim 1.

* * * * *

UNITED STATES PATENT AND TRADEMARK OFFICE
CERTIFICATE OF CORRECTION

PATENT NO. : 8,084,430 B2
APPLICATION NO. : 12/160359
DATED : December 27, 2011
INVENTOR(S) : Liu et al.

It is certified that error appears in the above-identified patent and that said Letters Patent is hereby corrected as shown below:

Title page, (75) Inventors: "Zhengzhou Liu," should read --Zhenzhong Liu,--.

Col. 10, line 37, claim 1: Claim 1 should be renumbered as claim 4.

Col. 11, line 19, claim 4: Claim 4 should be renumbered as claim 1.

Col. 11, line 37, claim 5: Claim 5 is to depend on renumbered claim 4. "claim 1" should read --claim 4--.

Col. 12, line 59, claim 10: Claim 10 is to depend on renumbered claim 4. "claim 1" should read --claim 4--.

Signed and Sealed this
Nineteenth Day of June, 2012

David J. Kappos
*Director of the United States Patent and Trademark Office*